US00PP29377P2

(12) United States Plant Patent
Hansen

(10) Patent No.: US PP29,377 P2
(45) Date of Patent: Jun. 12, 2018

(54) ***VERONICA* PLANT NAMED 'ROYAL REMBRANDT'**

(50) Latin Name: ***Veronica spicata* L.**
Varietal Denomination: Royal Rembrandt

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 6 days.

(21) Appl. No.: 15/530,509

(22) Filed: Jan. 23, 2017

(51) Int. Cl.
*A01H 5/02* (2018.01)

(52) U.S. Cl.
USPC ..... Plt./251

(58) Field of Classification Search
USPC ..... Plt./251
See application file for complete search history.

*Primary Examiner* — Anne Marie Grunberg

(57) ABSTRACT

The new and distinct cultivar of ornamental spike speedwell plant, *Veronica* 'Royal Rembrandt', with tight mounded habit and stiff freely-branched branched spikes producing violet-purple flowers over a long period beginning early summer and repeating into early fall. Flowers first year from cuttings without vernalization, but vernalization may be beneficial.

1 Drawing Sheet

Botanical classification: *Veronica spicata* L.
Variety denomination: 'Royal Rembrandt'.

BACKGROUND OF THE INVENTION

The present invention relates to the new and distinct cultivar of spike speedwell, botanically known as *Veronica spicata* 'Royal Rembrandt', and hereinafter referred to as the cultivar 'Royal Rembrandt' or the "new plant". The new plant was hybridized in the summer of 2012 by the inventor at a wholesale perennial nursery in Zeeland, Mich., USA, with the proprietary unreleased seedling known only by the breeder code 08-64-01B as the female parent and 'Enchanted Indigo' U.S. Plant Pat. No. 26,603 as the male parent. The cross was performed on Jun. 29, 2012 and the individual seedling that was ultimately named 'Royal Rembrandt' was identified by the breeder code 12-35-01 throughout the trial period.

The new plant has been asexually propagated by shoot tip cuttings at the same nursery in the greenhouses in Zeeland, Mich., since the summer of 2014 with subsequent asexually propagated plants found to be identical to the original selection with all the same traits as the original seedling.

No plants of *Veronica* 'Royal Rembrandt' have been sold or disclosed by this or any other name, in this country or anywhere in the world, prior to one year from the filing of this application, with the exception of that was sold or disclosed within one year of the filing of this application and which was either derived directly or indirectly from the inventor.

BRIEF SUMMARY OF THE PLANT

*Veronica spicata* 'Royal Rembrandt' is unique from all other spike speedwell known to the inventor. Several other cultivars may have some similar traits, but this is the only variety known by the inventor to have the following characteristic combinations that establish the new plant as unique:

1. Tight mounded habit with stiff spikes above dense mats of foliage.
2. Scapes with numerous flowers of distinctly violet-purple petals.
3. Freely branched peduncles with long blooming season.
4. Flowers first year without vernalization from cuttings, but vernalization may be beneficial.

The closest comparison varieties to the new plant are 'Enchanted Indigo', 'Sunny Border Blue' (not patented), 'Goodness Grows' (not patented), 'Atomic Violet' U.S. Plant Pat. No. 21,780 and 'Atomic Blue' U.S. Plant Pat. No. 21,840. The new plant is more upright and has taller spikes and is also wider than 'Atomic Blue' and much taller and wider than 'Goodness Grows'. 'Atomic Violet' has close to the same height, but about half the clump width. The flowers of 'Royal Rembrandt' is closer to the blue hue than 'Atomic Violet' and closer to the violet hue than 'Sunny Border Blue', 'Atomic Blue', 'Goodness Grows' and 'Enchanted Indigo'. Compared with the female parent the new plant has more violet-purple flowers.

BRIEF DESCRIPTION OF THE DRAWINGS

The photograph of the new plant demonstrates the overall appearance and unique traits of 'Royal Rembrandt' as a two-year-old plant grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
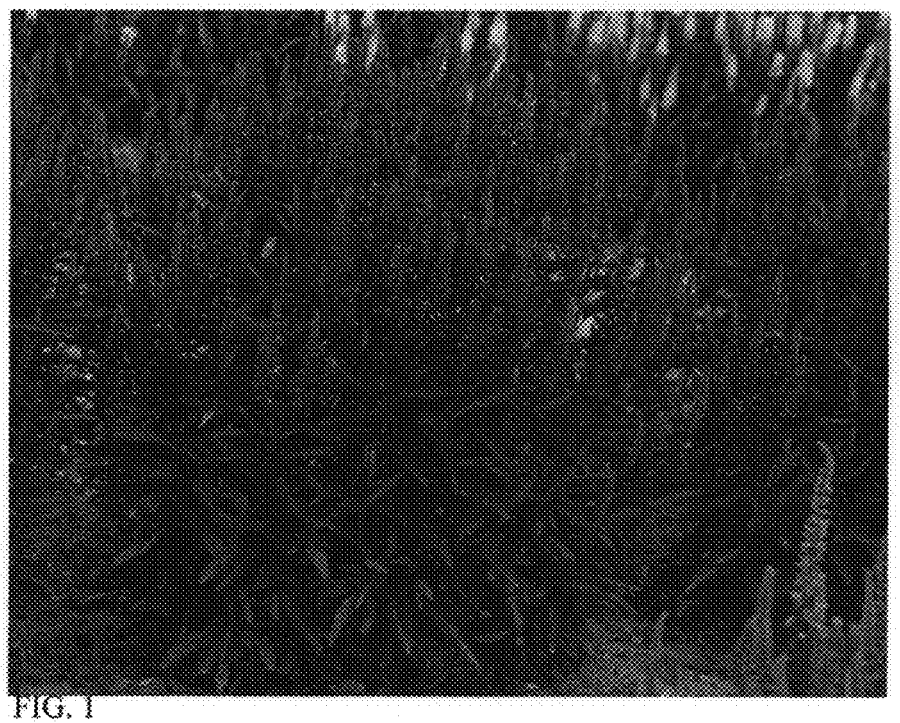
FIG. 1 shows the habit of the new plant in full flower.
Figure 2:
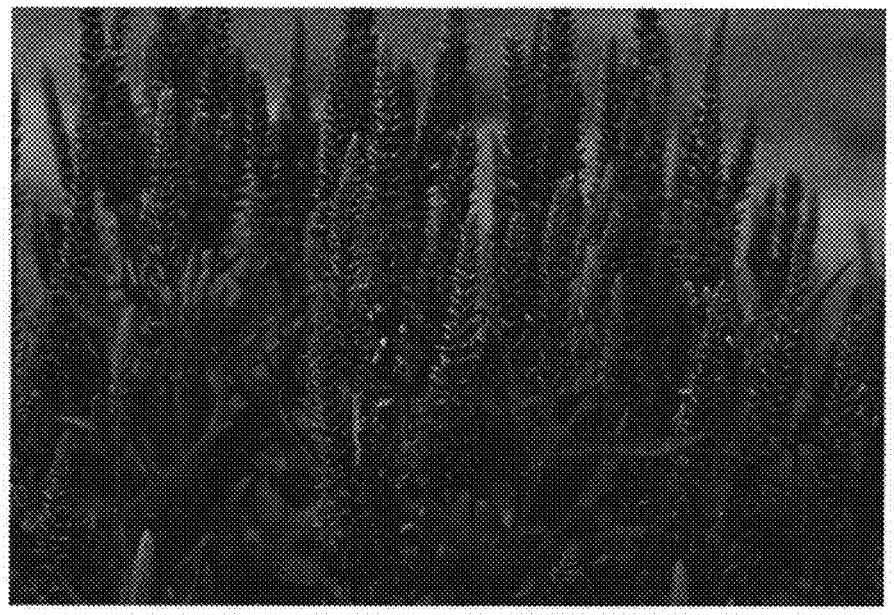
FIG. 2 shows a close-up of the flowers and buds.

The following descriptions and color references of a greenhouse-grown two-year-old plant of *Veronica* 'Royal Rembrandt' are based on the 2001 edition of The Royal Horticultural Society Colour Chart except where common dictionary terms are used. *Veronica* 'Royal Rembrandt' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a nursery in Zeeland, Mich. with supplemental fertilizer and water as needed.

Botanical classification: *Veronica spicata;*

Parentage: Female (seed parent) the plant identified by proprietary breeder code 08-64-01B; male (pollen parent) 'Enchanted Indigo';

Plant habit: Hardy herbaceous perennial, with rounded habit, average 50 freely-branched stems, main stems blooming to about 49.0 cm tall and clumping to about 55 cm across; flowering beginning late June in Michigan continuing for about 4 to 6 weeks and repeating later in early fall, especially if deadheaded;

Leaves: Simple; flat; lanceolate; opposite; serrated margin with about three to four teeth per one centimeter; glabrous abaxial and adaxial, acute apex, attenuate base; about 5.2 cm long by 1.2 cm wide decreasing in both length and width distally;

Leaf color: Mature leaves adaxial nearest RHS 139A; abaxial nearest RHS 137B; young expanding leaves nearest RHS 146B abaxial and adaxial;

Veins: Reticulate; sparsely micro-puberulent adaxial; glabrate to glabrous adaxial; abaxial midrib costate, about 1.0 mm across at abaxial base and about 0.5 mm at adaxial base;

Vein color: Adaxial midrib nearest RHS 146D and secondary veins nearest RHS 139A; abaxial midrib nearest RHS 146D with secondary veins nearest RHS 137A;

Petiole: Simple, slightly concaved upward on edges, margin minutely ciliate; about 3.0 mm long and 2.5 mm wide length shorter and narrower on distal leaves;

Petiole color: Adaxial base nearest RHS 146D, distally nearest 139A; abaxial nearest RNS 137B with base nearest RHS 146C;

Buds one to two days prior to opening: Convolute, narrowly oblong, obtuse apex; about 5.8 mm long and 2.5 mm diameter;

Bud color: Nearest RHS 96B with base nearest RHS 85C;

Flowers: On heavily branched upright spikes in compressed conglomerate; numerous; zygomorphic; campanulate; approximately 260 per main spike; about 9.0 mm long and about 7.0 mm across; flowers persist individually for 4 to 6 days whether on the plant or cut; petals self-cleaning, sepals and style persistent;

Flower timing: Early to mid-summer and repeating if deadheaded into early fall;

Flower fragrance: None detected;

Petals: Four; one larger petal above and three slightly smaller below and to either side; simple, entire, fused in basal 3.5 mm; glabrous abaxial and pubescent with 1.0 mm long white hairs in tuft band about 1.0 to 2.0 mm from adaxial base; upper larger petal with acute apex, about 7.0 mm long by 3.0 mm wide; side and lower petals with acute apex, about 7.0 mm long and 1.5 mm wide;

Petal color: Abaxial nearest RHS 86A and adaxial nearest RHS 86A with abaxial and adaxial base lighter than N87D or RHS 85D; with hairs inside tube white, whiter than RHS 155D;

Androecium:

*Filaments*.—Two; divergent; glabrous; epipetalous about 1.0 mm from base; about 5.5 mm long by about 0.25 mm diameter; color nearest RHS N87A.

*Anther*.—Dorsifixed, longitudinal; ellipsoid, with acute apex and rounded base; about 1.5 mm by 1.0 mm; color nearest RHS 83A.

*Pollen*.—Abundant, globose, less than 0.1 mm; nearest RHS 4C.

Gynoecium: Single, superior; persists after petal drop;

*Style*.—Straight; attitude mostly outwardly; about 7.0 mm long and 0.25 mm diameter; color nearest RHS 83B.

*Stigma*.—Globose; finely puberulent; about 0.3 mm in diameter; color RHS 83A.

*Ovary*.—Spherical to slightly elliptic; about 1.0 mm long and 0.8 mm in diameter; color nearest RHS 145B.

Sepals: Four, surface dull, ovate to narrowly ovate, acute apex, base fused forming campanulate calyx, puberulent margin; adaxial glabrous; abaxial nearly microscopically puberulent; about 4.0 mm long and 1.5 mm across;

Sepal color: Abaxial and adaxial nearest RHS 138A;

Peduncle: Strong, erect, branched at nodes; terete; puberulent; flowering portion about 16 cm long, 2.5 cm wide with stem 2.5 mm in diameter at the base; attitude upwardly; freely branching at distal nodes; about 7 to 8 nodes before flowers; average internode length about 2.8 cm;

Peduncle color: Between RHS 146A and RHS 137C;

Pedicel: Rigid, about 1.0 mm long and 0.3 mm wide, finely puberulent; attitude mostly outwardly;

Pedicel color: Nearest RHS 138A;

Bract: One, subtending each flower, linear; acute apex; margin entire; sessile, based sessile, attenuate; proximal bracts about 5.0 mm long and 1.0 mm wide decreasing distally;

Bract color: Adaxial and abaxial nearest RHS 137B;

Fruit: Ellipsoid, rounded apex and base; about 3.1 mm long and 2.5 mm across; color between RHS 166A and RHS 166B;

Propagation: The plant roots from cuttings in about 2 weeks and finishes to flowering in a 3.8 liter container in 8 to 10 weeks following a vernalization period of about 8 weeks, but vernalization not required to flower;

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other spike speedwell has not been observed.

It is claimed:

1. A new and distinct cultivar of ornamental spike speedwell plant, *Veronica* 'Royal Rembrandt', as herein described and illustrated.

* * * * *